United States Patent [19]

Scott

[11] Patent Number: 4,850,343

[45] **Date of Patent: * Jul. 25, 1989**

[54] ASSIST HANDLE FOR CHIROPRACTIC TREATMENT TABLE

[75] Inventor: Gerald R. Scott, Elmhurst, Ill.

[73] Assignee: Standex International, Salem, N.H.

[ * ] Notice: The portion of the term of this patent subsequent to Feb. 2, 2005 has been disclaimed.

[21] Appl. No.: 149,522

[22] Filed: Jan. 28, 1988

Related U.S. Application Data

[63] Continuation-in-part of Ser. No. 780,303, Sep. 26, 1985, Pat. No. 4,722,328.

[51] Int. Cl.⁴ ................................................ A61F 5/01

[52] U.S. Cl. ........................................ 128/74; 128/70

[58] Field of Search .................................. 128/70–75, 128/69, 80 R; 269/323–328; 272/144, 145, 903, 72, 117, 118

[56] References Cited

U.S. PATENT DOCUMENTS

| | | | |
|---|---|---|---|
| 1,417,675 | 5/1922 | McManis | 128/74 |
| 1,710,475 | 4/1929 | Gallowitz | 269/325 |
| 1,735,569 | 11/1929 | Gregory | 128/71 |
| 1,851,630 | 3/1932 | Johnson | 403/62 |
| 1,874,424 | 8/1932 | Benson | 403/62 |
| 2,023,429 | 12/1935 | Lorang | 128/72 |
| 2,787,262 | 4/1957 | Warner | 128/71 |
| 4,180,254 | 12/1979 | Lee et al. | 269/328 |
| 4,535,762 | 8/1985 | Natchev | 128/71 |
| 4,649,905 | 3/1987 | Barnes | 128/74 |
| 4,722,328 | 2/1988 | Scott et al. | 128/74 |

*Primary Examiner*—David A. Wiecking
*Assistant Examiner*—Huong Q. Pham
*Attorney, Agent, or Firm*—Mason, Kolehmainen, Rathburn & Wyss

[57] ABSTRACT

An assist bar is provided for facilitating a standing chiropractor in the manipulative treatment of a prone patient's spine while the patient is supported on a leg support section of a chiropractic table of the type having a body support section for the patient's body pivotally interconnected with the leg support section. The assist bar includes a connector at one end for securing the bar to the leg support section remote from the pivotal interconnection of the section with the main body support section. The assist bar extends outwardly of the leg support section and a handle is provided adjacent an outer end portion for facilitating a chiropractor in manipulating the patient's lower body up and down or side to side while making adjustments in the patient's spine with the other hand on the patient's body on the body support section.

27 Claims, 7 Drawing Sheets

ASSIST HANDLE FOR CHIROPRACTIC TREATMENT TABLE

RELATED APPLICATION

The present application is a continuation-in-part of copending U.S. patent application Ser. No. 780,304, filed Sept. 26, 1985 for CHIROPRACTIC MANIPULATION TABLE, issued on Feb. 2, 1988 as U.S. Pat. No. 4,722,328.

BACKGROUND OF THE INVENTION

1. Field of the Invention

The present invention relates to a new and improved assist bar or handle for facilitating a standing chiropractor in the manipulative treatment of a prone patient's spine while the patient is supported on a leg support section of a chiropractic table of the type including a body support section for the patient's body pivotally interconnected with the leg support section.

2. Description of the Prior Art

U.S. Pat. Nos. 1,062,489; 1,386,901; 1,427,004; 2,208,502; 3,176,975; and 4,569,339 disclose patient treatment tables having separate sections for supporting a patient's body and his legs and the sections are adjustable relative to one another. U.S. Pat. Nos. 1,453,013 and 1,686,979 disclose treatment tables wherein separate leg support and body support table sections are pivotally interconnected for manipulative treatment of a patient lying on the table. U.S. Pat. No. 1,642,158 discloses a spinal adjustment device wherein a patient supporting table section is movable relative to foot and head restraint elements and is controlled by the patient himself by means of a lever for raising and lowering a pad supporting the patient's lower back.

However, none of the aforementioned prior art patents disclose a chiropractic treatment table wherein an assist bar is provided for facilitating a standing chiropractor in the manipulative treatment of a prone patient's spine while the patient is supported on a leg support section and a body support section which are pivotally interconnected to provide for relative angular manipulation between the patient's upper body and lower body.

OBJECTS OF THE INVENTION

Accordingly, it is an important object of the present invention to provide a new and improved assist bar or handle for facilitating a chiropractor in the manipulative treatment of a patient's spine while the patient is supported in a generally prone position on a chiropractic table of the type having a body support section and a leg support section pivotally interconnected so that the patient's lower body may be angularly manipulated relative to the upper body.

Another important object of the present invention is to provide a new and improved chiropractic treatment table of the character described having an assist bar or handle secured to a leg support section of the table for assisting a chiropractor in angular manipulation treatment of a patient's legs and spine.

It is another object of the present invention to provide a new and improved assist bar for a chiropractic treatment table which is detachable therefrom, when desired, and which may be secured to a leg support section of the table within a range of different positions relative to a pivotal interconnection point between the leg support section and the body support section of the table.

Yet another object of the present invention is to provide a new and improved assist bar for facilitating a chiropractor while standing adjacent a table in the angular manipulation of a patient's legs while making spinal adjustments on the patient's body.

Yet another object of the present invention is to provide a new and improved assist bar of the character described which reduces the amount of force required by the chiropractor for angular manipulation of the patient's spine and accordingly reduces chiropractor fatigue.

Yet another object of the present invention is to provide a new and improved assist bar of the character described which includes a pair of pivotally interconnected elongated sections which are pivotable between a folded-down condition for facilitating a patient in mounting and dismounting from the table and an upstanding position for patient treatment.

Yet another object of the present invention is to provide a new and improved assist bar of the character described wherein a handle is provided and the position of the handle relative to the pivotal interconnection between the body support section and a leg support section may be adjusted in a range of positions so as to provide convenience and ease of operation for a chiropractor during manipulative therapy.

BRIEF SUMMARY OF THE INVENTION

The foregoing and other objects and advantages of the present invention are accomplished in a new and improved assist bar for facilitating a chiropractor in the manipulation therapy of a prone patient's spine while the patient is supported on a chiropractic table of the type having a body support section pivotally interconnected with a leg support section so that the standing chiropractor may make simultaneous adjustments to the patient's spine while the patient's legs are being manipulated with the aid of the assist bar. The assist bar includes a connector assembly adjacent a lower end for detachably securing the bar to the leg support section of the table and project outwardly thereof. The assist bar also includes a handle adjacent an opposite end for convenience in grasping the assist bar to make angular adjustment when manipulating a patient's lower body relative to the patient's upper body while spinal adjustments are made by the chiropractor.

An alternate embodiment of the present invention comprises an assist bar of the character described having a plurality of elongated elements pivotally interconnected by a pivoted pin between the handle and the connector so that relative angular adjustment between the elements results in a range of positions of the handle relative to the leg support section of the table. A lower one of the elongated elements is also pivotally secured to the connector for pivotal movement relative to the leg support section of the table and a locking system is provided to lock the pivotally interconnected elements when a desired position is selected so that thereafter, the handle remains in a fixed position relative to the leg support section of the table for easier manipulation of the patient.

BRIEF DESCRIPTION OF THE DRAWINGS

For a better understanding of the invention, reference should be had to the following detailed description taken in conjunction with the drawings, in which.

DESCRIPTION OF THE PREFERRED EMBODIMENTS

Figure 1:
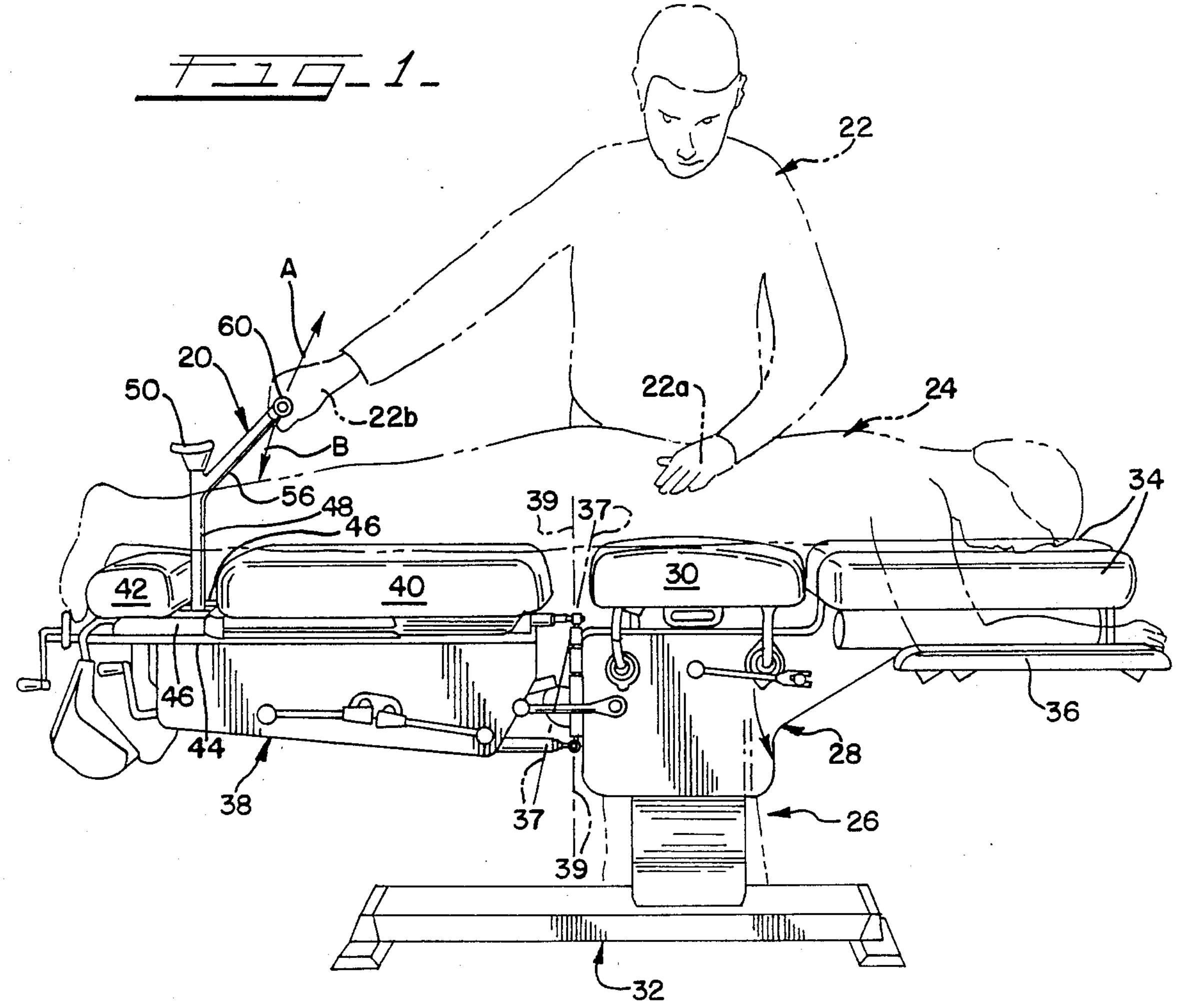
FIG. 1 is a side elevational view of a new and improved assist bar for facilitating a chiropractor in the manipulation of a patient while supported on a chiropractic table of the type having a body support section and a separate leg support section pivotally interconnected thereto constructed in accordance with the features of the present invention.

Referring now to the drawings and in particular FIGS. 1-5, therein is illustrated a new and improved assist bar or assist handle 20 constructed in accordance with the present invention and especially designed and adapted to facilitate a chiropractor 22 in the treatment of a patient 24 lying in a generally prone position on a chiropractic manipulation table 26 of the type shown and described in the aforementioned copending U.S. patent application, now U.S. Pat. No. 4,722,328.

As more fully described in the aforementioned copending U.S. patent application, the chiropractic treatment table 26 includes a body supporting central section 28 having a body support cushion 30 provided at a convenient working level about waist high above the floor and supported on a sturdy central base structure 32. As viewed in FIGS. 1 and 2 a right hand end portion of the body table section 28 provides support for the upper torso, head and arms of the patient and for this purpose, a head cushion 34 and a pair of arm rests 36 are provided.

As illustrated in FIG. 1, when the patient 24 is lying face down in a prone position ready for treatment on the table 26, the chiropractor 22 can make adjustments to the patient's spine with a left hand 22*a* at a convenient waist high working level directly in front. At the same time, a right hand 22*b* of the chiropractor may be conveniently extended outwardly to grasp the assist bar 20 by a laterally extending handle 60 at an upper end portion well above the level of the patient's legs which are being manipulated.

As more fully described in the aforementioned copending U.S. patent application, the chiropractic treatment table 26 is especially designed for caudal flexion distraction treatment of the patient 24 and for this purpose includes a separate leg support section 38 pivotally interconnected to the central, body supporting table section 28 for pivotal manipulation of the patient's legs about a horizontal lateral extending axis 37 as indicated by the arrows A and B.

Figure 2:
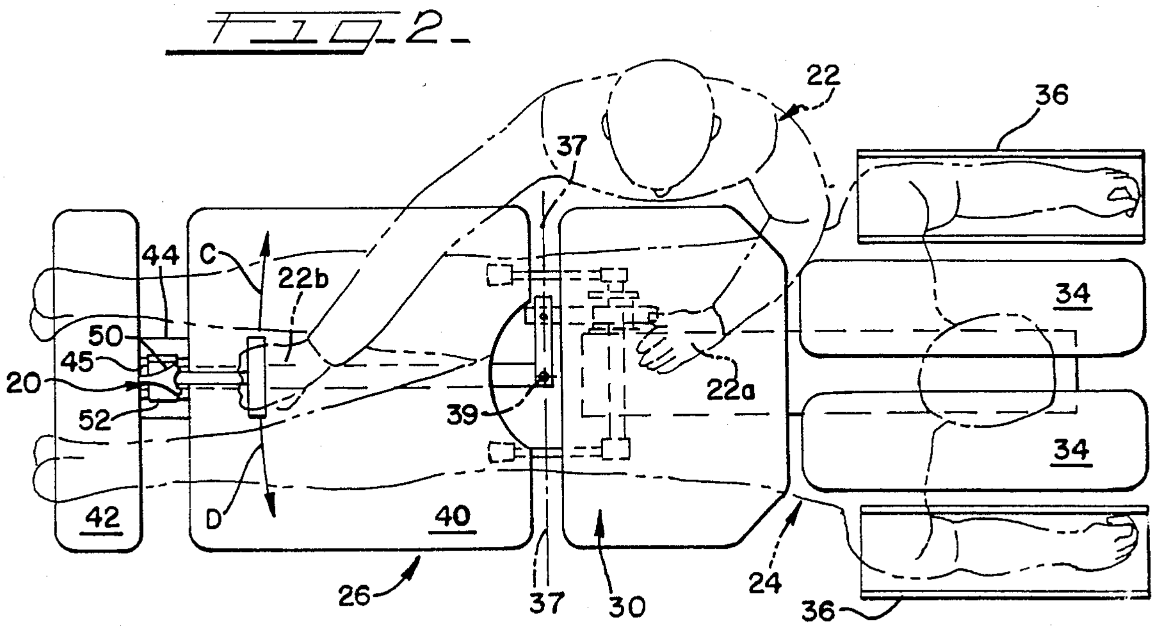
FIG. 2 is a plan view of the assist bar and table of FIG. 1 looking downwardly thereon and illustrating the position of the chiropractor's arms and hands during treatment of a patient lying on the table.

In addition, the leg support section 38 of the table may also be pivotally manipulated by the chiropractor 22 to move about a vertical axis 39 spaced between the separate table sections 28 and 38 so that the patient's legs may move in lateral flexion in relation to the patient's body or trunk as indicated by the arrows C and D (FIG. 2). The leg supporting table section 38 includes a leg supporting main cushion 40 and a longitudinally outwardly adjustable ankle support cushion 42 for accommodating both short and tall patients of different height.

In accordance with the present invention, the assist bar 20 is detachably connected to an undercarriage 44 of the leg support table section 38 and more particularly, is mounted to extend upwardly from a centrally disposed elongated longitudinal slot 45 defined on opposite edges by support plates 46 extending longitudinally of the table 26 between the pivot axes 37 and 39 on one end and the ankle support cushion 42 on the other. In the event that a tall patient is being treated, the assist bar 20 may be moved further outwardly away from the pivot axes 37 and 39 and when a shorter patient is treated, the assist bar may be moved inwardly as close as possible to abut the foot end of the leg support cushion 40 as illustrated in FIGS. 1 and 2.

The assist bar 20 includes an upstanding hollow column with a control knob 50 at the upper end and a detachable connector assembly at the lower end including a flat, rectangular or square shaped base plate 52 dimensioned to span across the transverse width of the slot 45. Intermediate the ends of the assist bar column, a branch socket 54 is attached to slope upwardly and outwardly in a direction toward the main body table section 28 and the pivot axes 37 and 39 so that the handle 60 is nearer to the chiropractor 22 than the point of attachment of the base 52 in the slot 45. The angle of slope is approximately a 45° angle relative to the support plates 46 of the leg support table section 38 and the socket supports an elongated hollow arm 56 which in turn supports the transverse tubular handle 60 at the upper end. The handle provides the chiropractor 22 with a convenient means for grasping the assist bar 20 to facilitate the angular manipulation of the leg support section 38 as desired. Normally, the detachable assist bar is centered between the legs of the patient 24 and the underside of the rectangular base plate 52 rests on the upper surface of the undercarriage 44 and is centered along the longitudinal center axis of the elongated slot 45.

The rotatable knob 50 at the upper end of the column 48 is threadedly connected to a rod 62 extending downwardly along the column center through an opening in the base plate 52 to support a rectangular lock plate 64 attached at the lower end of the rod. When unlocked the lock plate 64 has an upper surface spaced below the lower surface of the base plate 52 by a distance slightly greater than the thickness of the plates 46 of the undercarriage 44. To facilitate positioning of the assist bar in relation to the elongated slot 45, a pair of relatively short pins 66 are provided on the base plate 52 at diagonally opposite locations to extend downwardly from the underside of the base plate into the slot 45 between the opposite edges of the support plates 46.

Figure 5:
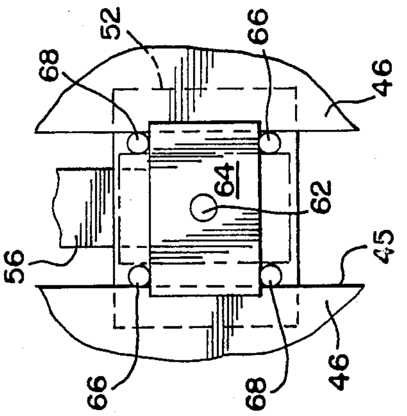
FIG. 5 is a fragmentary, cross-sectional view taken substantially along lines 5—5 of FIG. 3.
Figure 4:
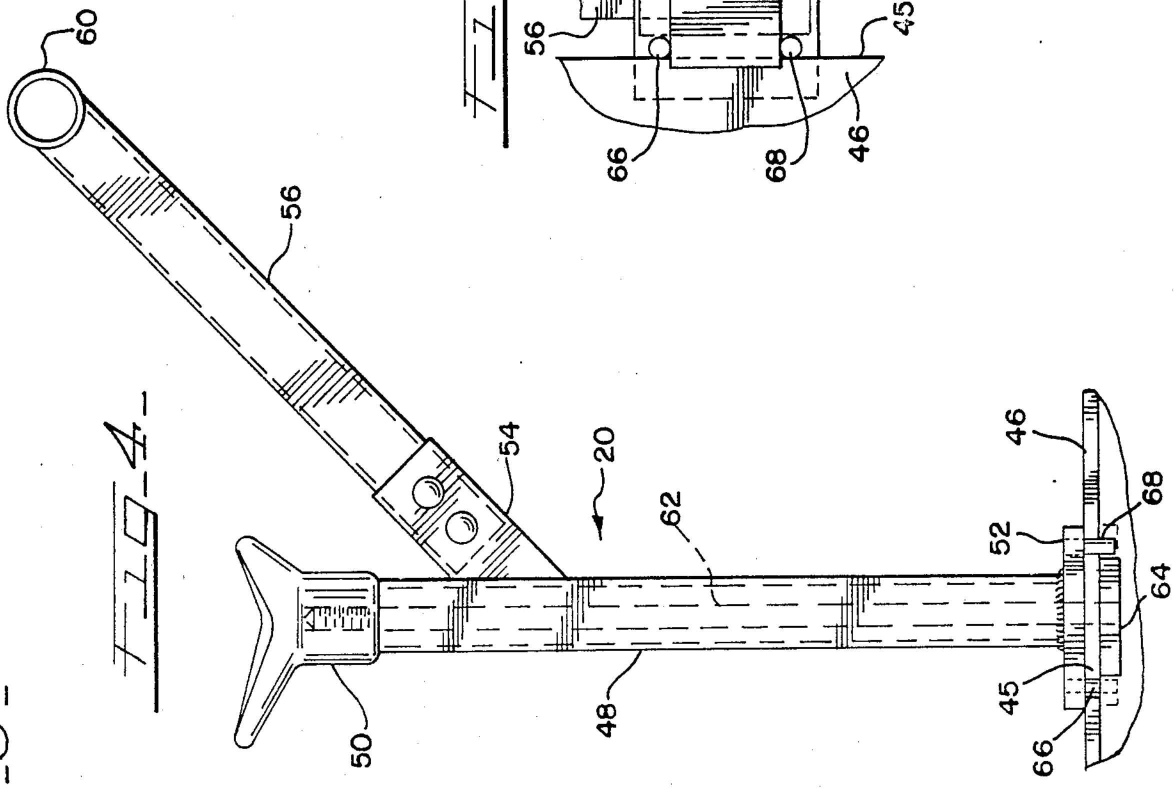
FIG. 4 is a side elevational view of the assist bar looking in the direction of arrows 4—4 of FIG. 3.
Figure 3:
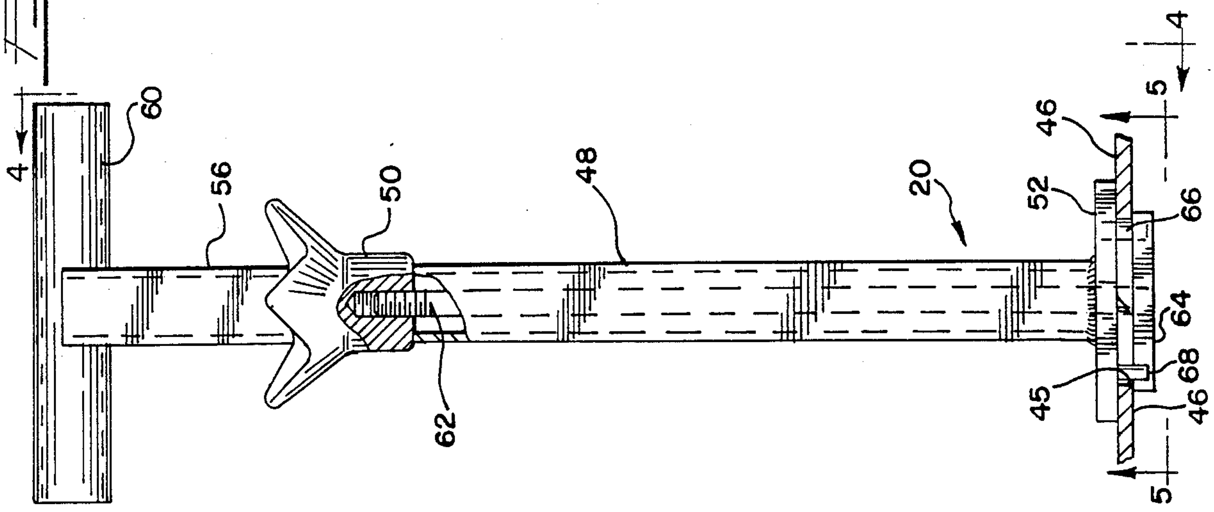
FIG. 3 is an enlarged, end elevational view of an assist bar constructed in accordance with the features of the present invention.

A pair of relatively long pins 68 are provided at opposite corner portions as best shown in FIG. 5 so that when the lock plate 64 is rotated 90° by the knob 50 the plate is movable between a locking position shown in solid lines in FIG. 5 wherein a longer central axis of the locking plate 64 is transversely positioned relative to the center axis of the slot 45 and a non-locking position shown in dotted lines wherein the longer central axis of the lock plate 64 is aligned parallel of the slot 45 and generally centered between the opposite sides edges of the support plates 46. The long pins 68 serve as stops for limiting rotational movement of the locking plate 64 beyond 90° between the locking and unlocking positions as illustrated. Further turning of the knob 50 when the lock plate 64 is in the locking position draws the lock plate upwardly against the underside of the plates 46 to firmly secure the assist bar 20 to the leg support section 38.

When it is desired to completely detach the assist bar 20, the knob 50 is turned to rotate the rod 62 and loosen the lock plate 64 and then rotate the plate from the transverse position back to the release position (dotted lines). When the longer axis of the plate 64 is aligned with the slot 45 the lock plate will clear the inside edges of the support plates 46 so that the assist bar can then be withdrawn upwardly from the undercarriage 44 of the leg supporting table section 38.

Because the slot 45 between the inside edges of the support plates 46 is substantially longer than the dimension of the lock plate 64, the assist bar 20 may be moved easily in a longitudinal direction along the slot and may be securely attached to the leg supporting table section 38 at a variety of different longitudinally spaced positions along the length of the slot outwardly of the pivotal interconnection between the separate table sections 28 and 38. The exact position of attachment is chosen so as to best facilitate a particular chiropractor 22 and a particular patient 24 for treatment in caudal flexion distraction and caudal swinging flexion in a lateral direction.

Figure 12:
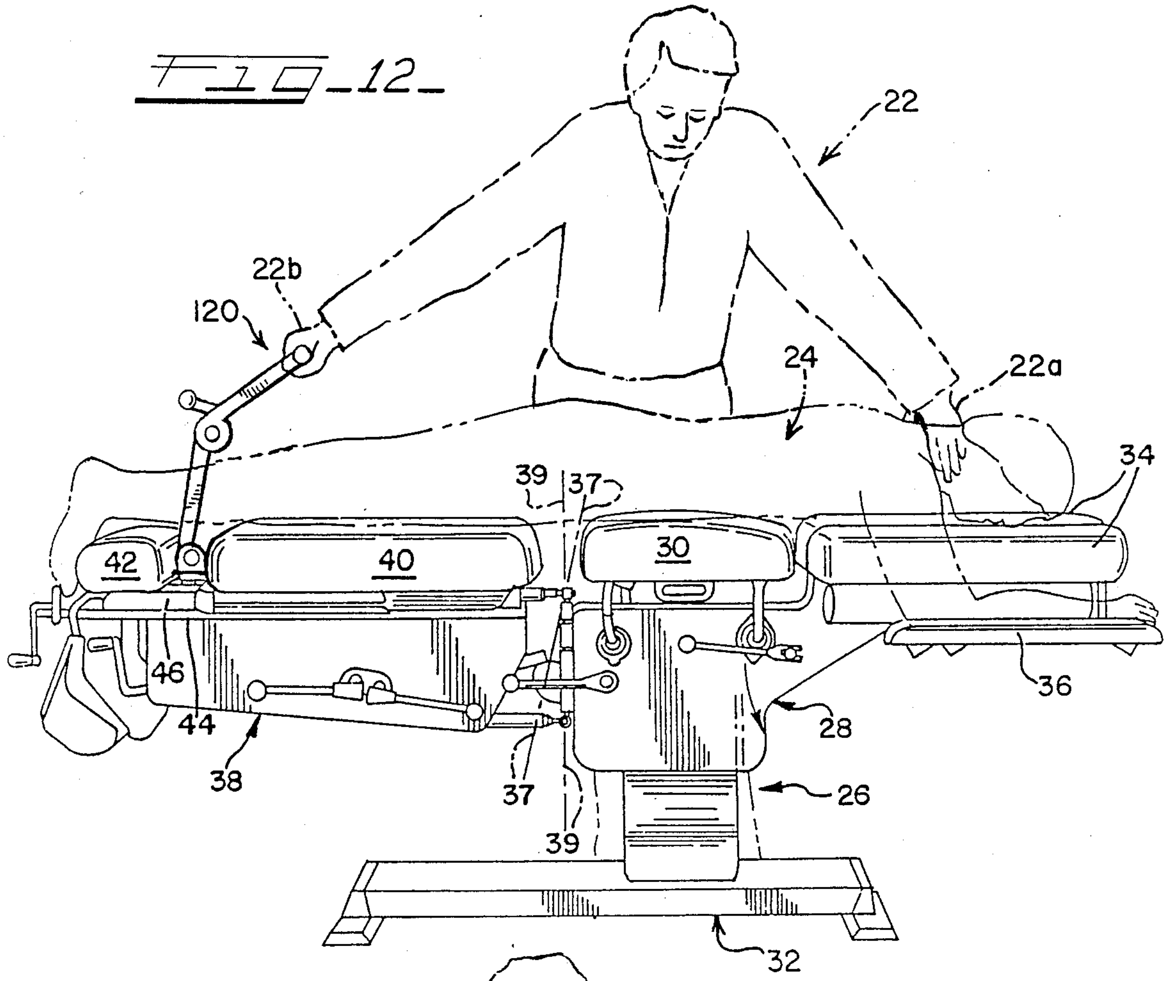
FIG. 12 is a front elevational view of a chiropractor while manipulating a patient on a chiropractic treatment table utilizing an assist bar in accordance with the invention.
Figure 13:
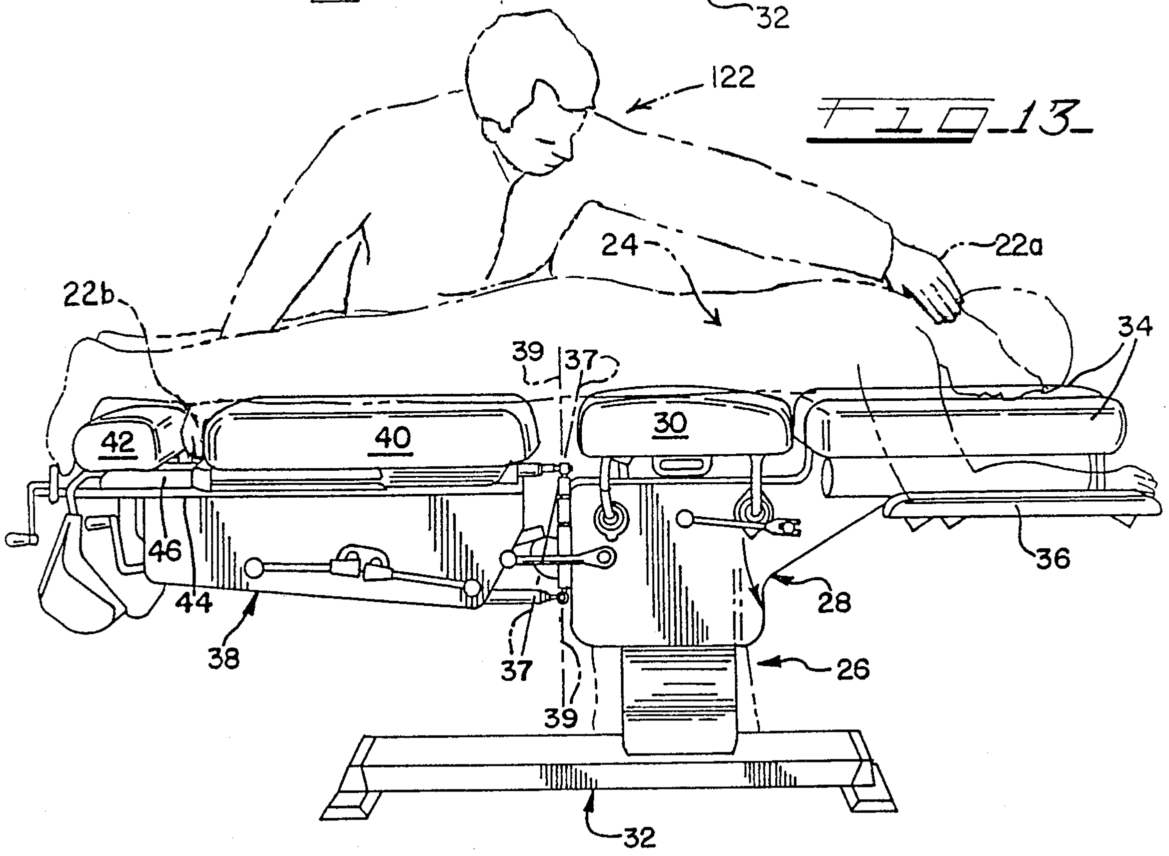
FIG. 13 is a view similar to FIG. 12 showing the greater reach required of a chiropractor while manipulating a patient on the treatment table without the advantage of the assist bar installed on the table.

When the manual assist bar 20 is attached to the leg supporting table section 38 of the chiropractic treatment table 26 as illustrated in FIGS. 1, 2 and 12, the assist handle 60 is positioned at a level well above the table section undercarriage 44 and above the patient's legs and thus reduces the reach otherwise required of the chiropractor 22 (FIG. 13) for angular manipulation of the patient's spine, both in caudal flexion distraction about the horizontal pivot axis 37 (as evidenced by the arrows A and B) and in lateral flexion about the vertical pivot axis 39 (as indicated by the arrows C and D) and when simultaneously angularly manipulating the patient's legs about both axes. Without the assist bar 20 in place as shown in FIG. 13, the chiropractor will have to reach out much further in order to grasp the undercarriage 44 or the patient's legs in order to effect the needed angular manipulation. This extended reaching as shown in FIG. 13 will adversely affect the chiropractor's ability to make simultaneous spinal adjustments on the patient's back, neck or lower torso with the other hand while the spinal manipulation takes place. Moreover, as illustrated in FIG. 13, without the assist bar in place, the chiropractor may have to bend over and strain while making spinal adjustments. When the patient 24 being treated is taller and/or larger than average size or when the chiropractor is shorter or less strong than the average, the reach factor becomes even more important and the assist bar 20 provides a much needed assist to the busy chiropractor.

With the assist bar 20 in place as shown, the handle 60 is spaced at or below the shoulder level of the average sized chiropractor and this position also reduces the arm force required of the chiropractor in angular manipulation treatment of the patient as described. The handle 60 is closer to the pivot axes 37 and 39 in a horizontal sense than is the point of attachment of the base plate 52 to the undercarriage 44 because of the 45° angle of the branch arm 56, and this factor aids in reducing the force and effort required of the chiropractor and reduces chiropractor fatigue.

An important factor in the treatment of a patient 24 while lying on the table 26 is the fact that simultaneous spinal adjustments that can be made on the patient's spine and torso with the left hand 22a of the chiropractor at a convenient working level about waist high and directly in front of the chiropractor while at the same time the patient's lower body is being angularly manipulated about the axes 37 and 39 effected by the chiropractor's right hand 22b grasping the handle 60 of the attached assist bar 20 at a higher level that is even with or slightly below the chiropractor's shoulders.

The manual assist bar 20, when attached to the leg supporting table section 38, provides for control of the leg supporting table section by the chiropractor 22. The handle 60 also provides an easily accessible place to grip the table structure to control rotational adjustment of the caudal cushion 40 around a horizontal axis, before treatment begins as described in the previously referenced copending U.S. patent application. The handle 60 further provides an easily accessible place to grip the table structure allowing the chiropractor to manipulate the leg supporting table section while providing treatment to the spinal area of the body. In addition, the use of the assist handle reduces possible patient embarrassment because the chiropractor does not have to reach between the patient's legs to grip the table structure for manipulation of the patient's lower body.

The detachable assist bar 20 of the treatment table 26 thus greatly facilitates the treatment of patients of all sizes in both caudal flexion distraction and in lateral flexion, while at the same time reducing the force and effort required, thereby reducing chiropractor fatigue. The assist bar is easily detached and removed from the table for facilitating the patient in mounting and dismounting from the table and is easily reattached and firmly secured in place on the table by the knob 50, even while a patient is lying on the table.

Referring now to FIGS. 6–11B, therein is illustrated another embodiment of a new and improved assist bar for the chiropractic treatment table 26 generally referred to by the reference numeral 120. The assist bar 120 includes a detachable connector assembly 122 for securing the assist bar in place on the undercarriage 44 of the leg support table section 38 of the chiropractic treatment table. The assist bar 120 need not be securable at different positions along the slot 45 like the assist bar 20 because of its unique design providing a range of relative angular positions relative to the undercarriage 44.

Figure 6:
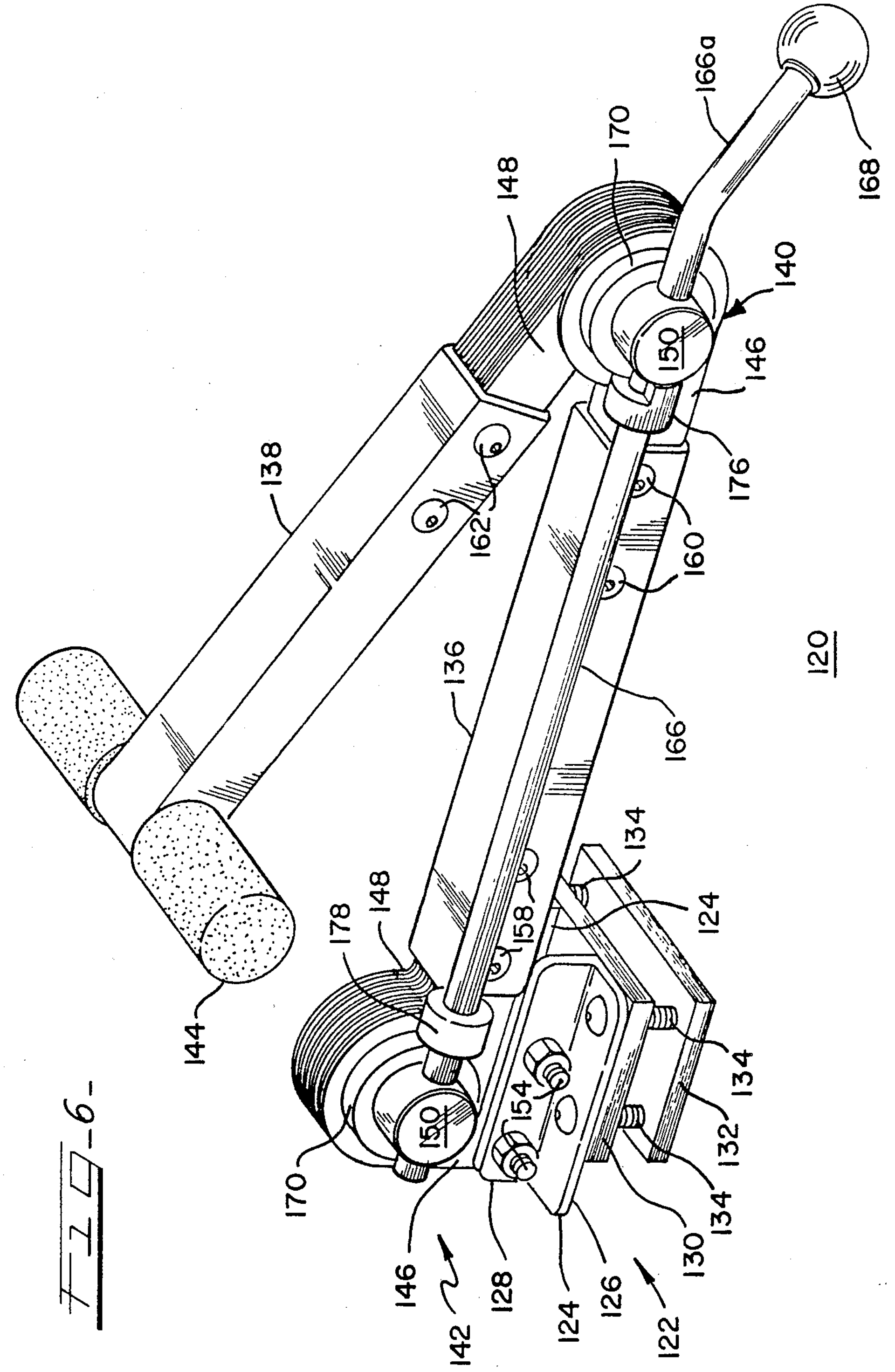
FIG. 6 is an enlarged perspective view of another embodiment of an assist bar in accordance with the present invention as shown in a folded-down condition for patient mounting and dismounting.
Figure 8:
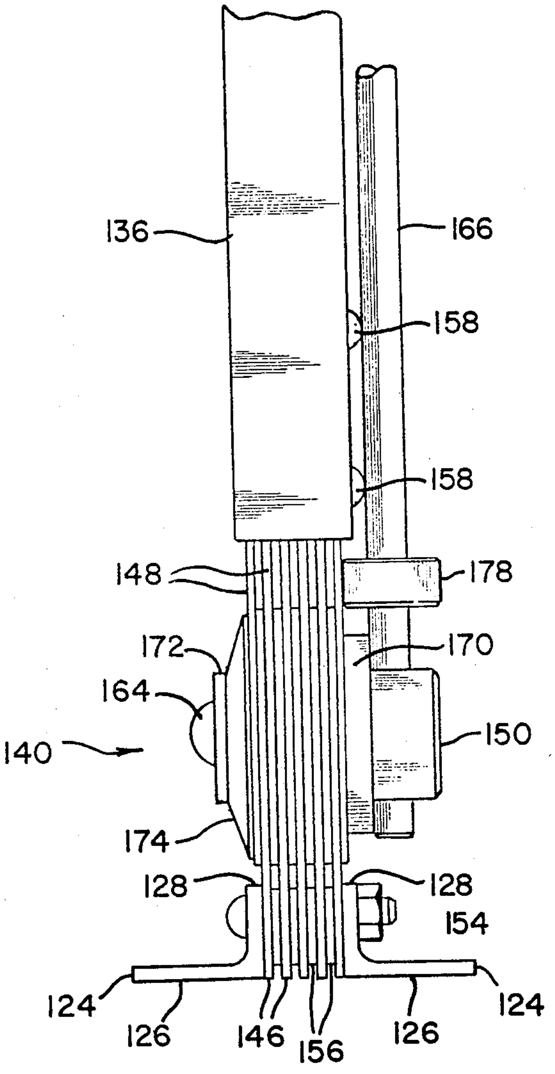
FIG. 8 is a fragmentary, end elevational view of the assist bar when illustrated in an upstanding position as shown in FIGS. 7A and 7B.

The connector assembly 122 includes a pair of angle bases 124 having lower horizontal flanges 126 and upstanding vertical flanges 128 in spaced apart parallel relation as best shown in FIGS. 6 and 8. The lower flanges 126 of the angles 124 rest upon a common mounting plate 130 of rectangular shape, which plate in turn rests on the upper surface of the elongated support plates 46. A tapped pressure or clamping plate 132 is provided below the support plates 46 and elongated threaded fasteners 134 are extended downwardly through openings in the flanges 126 and the plate 130 to be received in threaded, tapped openings provided in the pressure plate 132 so that when the fasteners are tightened, the pressure plate is clamped tightly against the underside of the undercarriage support plates 46 to firmly secure the connector assembly 122 in place in the slot 45 at the desired location.

Figures 7, 7A, 7B:
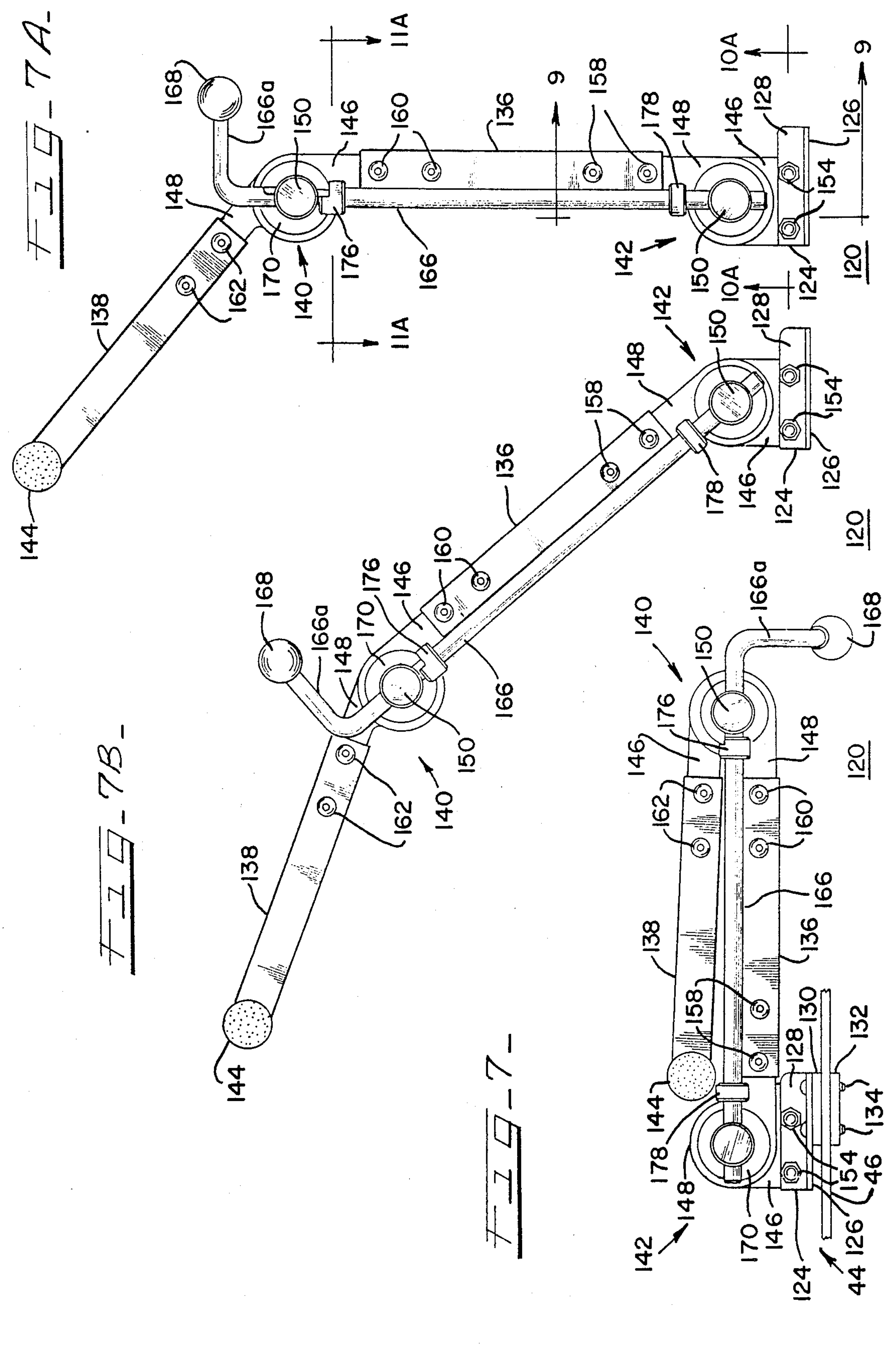
FIG. 7 is a side elevational view of the assist bar of FIG. 6 shown in the folded-down or down position.
FIG. 7A is a side elevational view of the assist bar as shown in an upstanding, extended position ready for use.
FIG. 7B is another side elevational view of the assist bar as shown in another angularly adjusted upstanding position ready for use.

In accordance with the present invention, the assist bar 120 includes a pair of elongated hollow tubular arm members 136 and 138 which are pivotally interconnected together at adjacent ends by a hinge assembly 140 in order to permit relative angular displacement between the arm members. The pivotal interconnection permits the assist bar to be folded-up as shown in FIGS. 6 and 7 for facilitating the patient in mounting and dismounting from the table 26. The arms 136 and 138 are also pivotal to provide a range of upstanding positions as shown in FIGS. 7A and 7B ready for manipulation of the patient during chiropractic treatment as previously described.

The lower end of the inner or lower elongated tubular arm member 136 is in turn pivotally interconnected to the angle bases 124 of the connector assembly 122 by a hinge assembly 142 generally similar to the hinge assembly 140. The outer end of the upper elongated tubular arm member 138 is provided with a transversely extending handle 144 generally similar to the handle 60 of the previous embodiment to provide for convenient grasping by the chiropractor during manipulative treatment.

Figure 9:
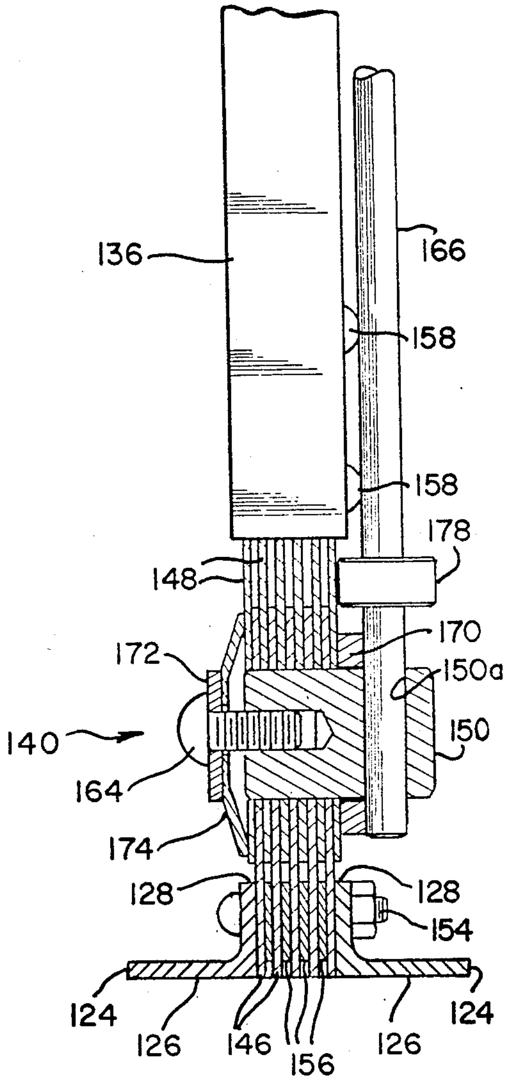
FIG. 9 is an enlarged, fragmentary cross-sectional view taken substantially along lines 9—9 of FIG. 7A.

The relative position of the handle 144 above the level of the undercarriage 44 of the leg support table section 38 is widely adjustable toward and away from the undercarriage and toward and away from the pivot axes 37 and 39 by virtue of the hinge assemblies 140 and 142 provided by the assist bar 120. The respective hinge assemblies 140 and 142 are substantially identical in function and each includes a pair of sets of spaced apart parallel hinge plates or leaves 146 and 148. Each hinge leaf is formed of thin sheet material having a large circular portion with a center aperture therein for receiving a pivot pin 150 extending transversely therethrough as best illustrated in FIG. 9. The leaf sets 146 and 148 of each hinge assembly 140 and 142 are alternately intermeshed between one another around the pivot pins 150 to provide a relatively large frictional contact surface for clamping tightly against one another when the leaves are pressed together while the hinge assemblies 140 and 142 are locked.

The lower set of hinge leaves 146 of the hinge assembly 142 are secured in an upstanding position between the flanges 128 of the base angles 124 by a pair of bolt and nut assemblies 154 and alternate spacer plates 156 are provided between the lower end portions of the hinge leaves. The spacer plates are slightly greater in thickness than the thickness of the hinge leaves. The upper set of hinge leaves 148 and alternate spacers (not shown) are secured in the interior of the lower end of the elongated tubular arm member 136 by a pair of fasteners 158. Similarly, the hinge leaves 146 of the hinge assembly 140 and spacers are secured in the elongated element 136 by fasteners 160 and the hinge leaves 148 and spacers are secured to the elongated element 138 by fasteners 162. Spacer plates 156 are thus provided between outer portions of the hinge leaves in each set 146 and 148 and are secured alternately between the leaves by the respective fasteners 154, 158, 160 and 162 in a fashion as shown in FIG. 9.

Each pivot pin 150 extends through large circular openings provided in alternately spaced hinge leaves of sets 146 and 148 as best shown in FIG. 9 and the pivot pins are provided with an axially aligned threaded bore at one end for receiving a cap screw 164 having an enlarged head and a threaded shank seated in the axial bore of the pivot pin. Each pivot pin also includes a transverse bore **150*a* adjacent an opposite end portion and spaced outwardly of the hinge leaves 146 and 148. The bores 150*a* of the respective pivot pins 150 of the hinge assemblies 140 and 142 are aligned along a common axis and a lock control rod 166** extends into and through each of the aligned bores to effect simultaneous control of the locking and unlocking of the hinge assemblies.

The locking control rod 166 includes an upper end **166*a* extended at right angles outwardly of the main body of the rod which remains generally parallel to the elongated tubular arm member 136. At the outer end, the transverse segment 166*a* is provided with a knob 168 for convenience in rotating the rod to pivot 90° about its longitudinal axis between alternate locking and unlocking positions as shown in FIGS. 11A and 11B**.

Each hinge assembly 140 and 142 is provided with a pair of large and small, annular pressure plates 170 and 172 on opposite ends to press inwardly against the intermeshing sets of hinge leaves 146 and 148. The smaller annular pressure plate 172 is engaged by the head surface of the cap screw 164 and in turn engages an inner portion of a "Bellville"-type spring washer 174 having an outer portion bearing against the central circular portion of the adjacent hinge leaf 146 or 148. On the opposite side of the intermeshing hinge leaves, the large annular pressure plate 170 bears inwardly against an adjacent hinge leaf and the biasing force of the "Belleville" washer normally tends to squeeze the sets of intermeshing leaves together.

Figure 10B:
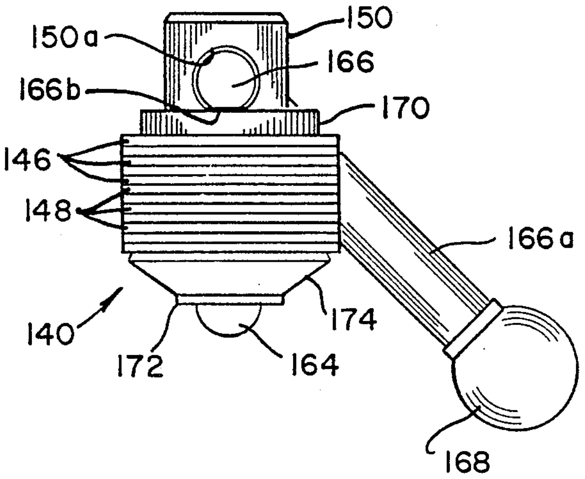
FIG. 10B is a cross-sectional view similar to FIG. 10A but illustrating the pivotal lock system in an unlocked position permitting angular adjustment of the elongated elements of the assist bar.
Figure 11B:
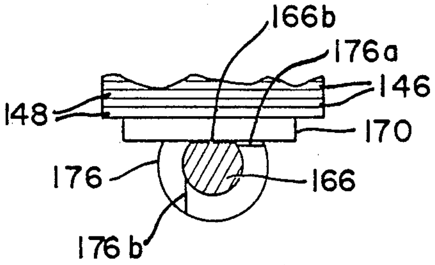
FIG. 11B is a fragmentary, enlarged cross-sectional view similar to FIG. 11A showing a lock stop element in an opposite stoppingly engaged position.

As illustrated in FIGS. 10A, 10B, 11A and 11B, the control rod 166 is provided with flat cam segments **166*b* in the otherwise cylindrical surface located adjacent the respective pivot pins 150 and seated within the transverse bores 150***a*. The control rod limits the movement of the pivot pins in a longitudinal direction under the influence of the "Belleville" spring washers 174 by engaging the outer surface of the large annular pressure plates 172. When the control rod 166 is rotated to an unlocked position as shown in FIGS. 10B and 11B, the flatted cam surfaces 166*b* are aligned to engage the outer surface of the large annular pressure plates 170 and this permits the pivot pins 150 to move longitudinally towards the cap screw end whereby the frictional forces applied by the "Belleville" washer 174 against the intermeshing hinge leaves 146 and 148 is greatly reduced. When this condition occurs, the elongated arm members 136 and 138 may be pivoted with minimal force about the pivot pin 150 of the hinge assembly 140 and the elongated tubular member 136 is similarly pivotal about the pivot pin 150 of the hinge assembly 142. A wide variety of relative angular positions may be attained so that the precise elevation of the handle 144 above the leg support table section 38 and the position of the handle relative to the pivot axis 37 in a horizontal sense can be selected as desired. Sufficient frictional contact between the intermeshing leaves 146 and 148 of each hinge assembly 140 and 142 is present even when the hinge assemblies are in an unlocked condition so that pivotal adjustment may be made and the members will remain in an adjusted position until the control rod 166 is operated to lock the hinge assemblies to firmly secure the arm members in the desired relationship ready for use.

Figure 10A:
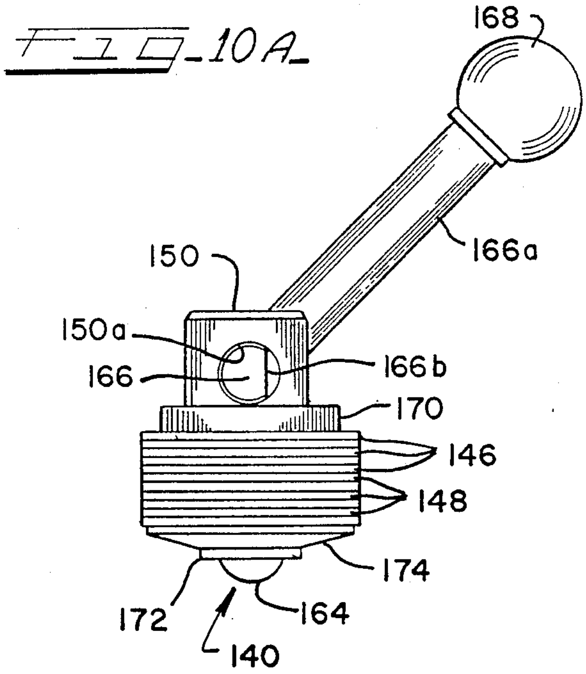
FIG. 10A is an enlarged, fragmentary cross-sectional viewing taken substantially along lines 10A—10A of FIG. 7A illustrating a pivotal lock system in a locked position.
Figure 11A:
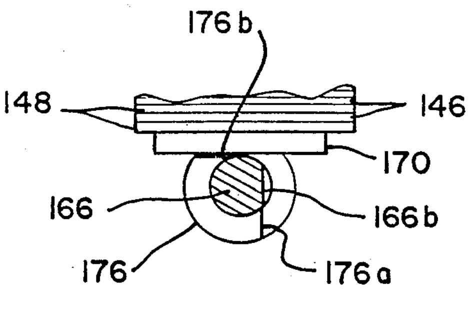
FIG. 11A is a cross-sectional view taken substantially along lines 11A—11A of FIG. 7A.

Once selected, the common control rod 166 is rotated approximately 90° by the arm 166*b* and the knob 168 into the locking position as shown in FIGS. 10A and 11A wherein the cylindrical surface of the rod engages the outer surface of the larger pressure plates 170 and pulls the pivot pins 150 in a direction away from the cap screws to exert locking pressure by the plate 170 and "Belleville" washer 174 against the set of alternate intermeshing hinge leaves 146 and 148. The single control rod 166 is thus effective to simultaneously lock and unlock the respective hinge assemblies 140 and 142.

Longitudinal displacement of the main body portion of the locking rod 166 is limited by a pair of upper and lower collars 176 and 178 as shown best in FIGS. 7, 7A, 11A and 11B. The upper collar 176 includes a notched out shoulder having flat surfaces 176*a* and 176*b* at right angles to one another and these surfaces are adapted to alternately engage the outer surface of the annular pressure plate 170 to limit rotational movement of the lock rod 166 to approximately 90°.

The assist bar 120 functions similarly to the assist bar 20 but additionally permits an infinite or fine adjustment of the precise position of the actuating handle 144 within a wide range of angular positions relative to the leg support structure 38. Also, the assist bar 120 need not be detached from the leg support structure 38 when not in use but can be pivoted into the folded-down condition as shown in FIG. 7 and locked therein. Only minimal obstruction is offered to a patient in dismounting and mounting on the chiropractic treatment table 26 when the assist bar 120 is locked in the folded-down position.

Many modifications and variations of the present invention are possible in light of the foregoing specification and thus, it is to be understood that within the scope of the appended claims, the invention may be practiced otherwise than as specifically described.

What is claimed and desired to be secured by Letters Patent of the United States is:

1. A chiropractor table comprising:
a body support section;
a leg support section;
pivotal connection means for connecting said body support section to said leg support section, said leg support section being pivoted about at least one support axis;
a movable assist bar having spaced apart end portions;
connection means for connecting one of said end portions of said bar to said leg support section, said assist bar including handle means at the other of said end portions located at an elevation above the level of said leg support section so as to be readily accessible to a chiropractor while a patient is supported on said table, said assist bar facilitating a standing chiropractor in manipulation of a patient's spine while the patient is lying on and supported by said chiropractic table by facilitating pivotal movement of said leg support section relative to said body support section about said axis to provide relative angular manipulation between the patient's upper body and lower body.

2. The assist bar of claim 1, wherein:
said connection means includes a pivot for permitting relative angular adjustment between said assist bar and said leg support section.

3. The assist bar of claim 1, wherein:
said connection means includes clamping means for securing said assist bar to said leg support section in a range of positions spaced from said pivotal connection means between said leg support section and said body support section.

4. The assist bar of claim 2, wherein said connection means includes releasable lock means for securing said assist bar to said leg support section in a selected relative angular position in said range.

5. The assist bar of claim 2, wherein said assist bar comprises:
a plurality of elongated elements pivotally interconnected by a pivot pin located between said handle means and said connection means for relative angular adjustment between said elements to raise and lower said handle means.

6. The assist bar of claim 5, including releasable lock means for securing said elements in a selected relative angular position.

7. The assist bar of claim 6, wherein:
said pivot of said connection means includes pivot means for permitting relative angular adjustment between said assist bar and said leg support section.

8. The assist bar of claim 7, including another releasable lock means for securing said assist bar in a selected angular position relative to said leg support section.

9. The assist bar of claim 8, including:
a common lock operator for simultaneously locking and unlocking both of said releasable lock means.

10. The assist bar of claim 9, wherein:
both of said releasable lock means includes means engagable with said pivot pin and with said pivot means for preventing relative angular movement between said elongated elements and between said assist bar and said leg support section respectively when locked and permitting relative angular adjustment when unlocked.

11. The table of claim 1, wherein said handle means is spaced above said leg support section for reducing the amount of reach required to manipulate the patient's lower body relative to the torso.

12. The table of claim 1, wherein said assist bar includes means permitting movement of said assist bar relative to a leg supporting surface of said leg support section for facilitating a patient in mounting and dismounting from said table.

13. The table of claim 1, wherein said handle means is supported for movement toward and away from said body support section for reducing the reach required of a chiropractor standing adjacent said body support section while angularly manipulating said patient's lower body on said leg support section.

14. The table of claim 1, wherein said one end portion of said assist bar is secured to said leg support section at a point remotely of said pivotal connection means and said other end portion is at a level above a patient's legs supported on said leg support section.

15. The table of claim 14, wherein said other end portion of said assist bar is spaced closer to said body support section than said one end portion for reducing the reach required of a chiropractor standing adjacent said body support section for manipulation of said leg support section.

16. The table of claim 14, wherein said connection means includes a detachable connector for securing said one end portion of said assist bar to said leg support section.

17. The table of claim 14, wherein said connection means includes means for securing said assist bar at a selected point on said leg support section for positioning said other end portion within a range of different distances away from said body support section.

18. The table of claim 1, wherein said pivotal connection means includes first pivot means permitting pivotal movement of said leg support section about a generally horizontal axis extending laterally of a longitudinal axis and extending between said sections, and wherein said assist bar extends above the level of said horizontal axis remote therefrom.

19. The table of claim 18, wherein said pivotal connection means includes second pivot means permitting pivotal movement of said leg support section about a generally upstanding axis between said sections.

20. The table of claim 11, wherein:

said assist bar includes a pair of upper and lower elongated members pivotally interconnected by a pivot pin for relative angular adjustment, an upper one of said members supporting said handle means and a lower one of said members connected to said leg support section, whereby by said relative angular adjustment between said members determines the position of said handle means relative to said sections.

21. The table of claim 20, wherein said lower member is pivotally interconnected for angular adjustment with said leg support section by a second pivot pin.

22. The table of claim 21, including:

lock means for securing the selected relative angular adjustment between said lower and upper members and between said lower member and said leg support section.

23. The table of claim 22, wherein:

said lock means includes a unitary lock element movable between locking and unlocking positions for simultaneous locking and unlocking said lower and upper members and said lower member and said leg support section in a selected relative angular adjustment.

24. The table of claim 1, wherein said handle means is positioned closer to said body support section than a point of attachment of said assist bar on said leg support section.

25. The table of claim 1, wherein:

said assist bar includes a plurality of elongated elements pivotally interconnected by a first pivot pin for relative angular adjustment and pivotally interconnected with said leg support section with a second pivot pin for relative angular adjustment, whereby said assist bar is movable between a folded-down position with said elongated elements generally parallel of said leg support section for patient mounting and dismounting and an extended position wherein said handle means is spaced above the legs of the patient lying on the table for manipulation.

26. The table of claim 25, including:

locking means for securing a selected position of relative angular adjustment between said elongated elements about said first pivot pin.

27. The table of claim 26, wherein:

said locking means includes means for securing a selected position of relative angular adjustment between said assist bar and said leg support section about said second pivot pin.

* * * * *

UNITED STATES PATENT AND TRADEMARK OFFICE
CERTIFICATE OF CORRECTION

PATENT NO. : 4,850,343

DATED : July 25, 1989

INVENTOR(S) : GERALD R. SCOTT

It is certified that error appears in the above-identified patent and that said Letters Patent is hereby corrected as shown below:

Cover Page - Under Related U.S. Application Data

[63] "Ser. No. 780,303" should read

-- Ser. No. 780,304 --.

Signed and Sealed this

Twenty-fifth Day of February, 1992

*Attest:*

HARRY F. MANBECK, JR.

*Attesting Officer* *Commissioner of Patents and Trademarks*